(12) United States Patent
Moeller et al.

(10) Patent No.: US 9,243,056 B2
(45) Date of Patent: *Jan. 26, 2016

(54) PROCESS FOR PREPARING AN IMMUNOGLOBULIN COMPOSITION

(71) Applicant: BIOTEST AG, Dreieich (DE)

(72) Inventors: Wolfgang Moeller, Oberursel (DE); Dieter Rudnick, Dreieich (DE); Oliver Maneg, Bad Homburg (DE); Michael Rodemer, Rodgau (DE); Herbert Dichtelmueller, Sulzbach (DE); Eckhard Flechsig, Dietzenbach (DE)

(73) Assignee: BIOTEST AG, Dreieich (DE)

( * ) Notice: Subject to any disclaimer, the term of this patent is extended or adjusted under 35 U.S.C. 154(b) by 249 days.

This patent is subject to a terminal disclaimer.

(21) Appl. No.: 13/655,649

(22) Filed: Oct. 19, 2012

(65) Prior Publication Data

US 2013/0052208 A1    Feb. 28, 2013

Related U.S. Application Data

(63) Continuation of application No. PCT/EP2011/056486, filed on Apr. 21, 2011.

(30) Foreign Application Priority Data

Apr. 22, 2010  (GB) .................................. 1006753.6

(51) Int. Cl.
| | | |
|---|---|---|
| C07K 1/30 | (2006.01) | |
| C07K 16/06 | (2006.01) | |
| A61K 9/00 | (2006.01) | |
| C07K 16/12 | (2006.01) | |
| A61K 39/395 | (2006.01) | |
| A61K 47/18 | (2006.01) | |
| C07K 16/14 | (2006.01) | |
| A61K 39/00 | (2006.01) | |

(52) U.S. Cl.
CPC .......... *C07K 16/1275* (2013.01); *A61K 9/0019* (2013.01); *A61K 39/39591* (2013.01); *A61K 47/183* (2013.01); *C07K 16/065* (2013.01); *C07K 16/121* (2013.01); *C07K 16/125* (2013.01); *C07K 16/1232* (2013.01); *C07K 16/1267* (2013.01); *C07K 16/14* (2013.01); *A61K 2039/507* (2013.01); *C07K 1/30* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,318,902 A | 3/1982 | Stephan | |
| 5,075,425 A | 12/1991 | Kotitschke et al. | |
| 5,190,752 A | 3/1993 | Moller et al. | |
| 5,256,771 A | 10/1993 | Tsay et al. | |
| 5,367,054 A * | 11/1994 | Lee ............................. 530/359 |
| 5,410,025 A | 4/1995 | Möller et al. | |
| 5,510,465 A | 4/1996 | Tsay et al. | |
| 5,612,033 A | 3/1997 | Tsay et al. | |
| 6,136,312 A | 10/2000 | Rentsch | |
| 6,190,608 B1 | 2/2001 | Laub et al. | |
| 6,833,108 B2 | 12/2004 | Laub et al. | |
| 7,186,410 B2 | 3/2007 | Chtourou et al. | |
| 7,553,938 B2 * | 6/2009 | Buchacher et al. ........ 530/390.1 |
| 7,727,974 B2 | 6/2010 | Kawano et al. | |
| 7,771,725 B2 | 8/2010 | Schmitthaeusler | |
| 2003/0152966 A1 | 8/2003 | Alred et al. | |
| 2006/0165686 A1 | 7/2006 | Elson et al. | |
| 2007/0072824 A1 | 3/2007 | Kawano et al. | |
| 2007/0105092 A1 | 5/2007 | Paul et al. | |
| 2008/0219969 A1 | 9/2008 | Schmitthaeusler | |
| 2009/0041780 A1 | 2/2009 | Schmitthaeusler | |
| 2013/0045199 A1 | 2/2013 | Moeller et al. | |

FOREIGN PATENT DOCUMENTS

| | | |
|---|---|---|
| CA | 2185617 | 3/1997 |
| CA | 2225470 | 12/1997 |
| CA | 2647506 | 10/2007 |
| EP | 0013901 | 8/1980 |
| EP | 0345543 | 12/1989 |
| EP | 0352500 | 1/1990 |
| EP | 0413187 | 2/1991 |
| EP | 0413188 | 2/1991 |
| EP | 0450412 | 10/1991 |
| EP | 0835880 | 4/1998 |
| JP | 2009-531400 | 9/2009 |
| JP | 2009-531401 | 9/2009 |
| RU | 2178309 C2 | 1/2002 |
| RU | 2255766 C2 | 7/2005 |
| RU | 2457863 C2 | 8/2008 |
| RU | 2457861 C2 | 8/2012 |
| WO | WO99/64462 | 12/1999 |

(Continued)

OTHER PUBLICATIONS

Caillet-Fauquet et al. (J. Virological Methods 118 (2004) 131-139.*
Radosevich (Vox Anguinis, 98, pp. 12-26, published online Jul. 2009).*
Nuesch et al. (Virology 331 (2005) 159-174).*
Burnouf, T., "Modern Plasma Fractionation," Transfusion Med. Rev. 2007;21(2):101-117.
Polosukhina, D., et al., "Hydrolysis of myelin basic protein by IgM and IgA antibodies from the sera of patents with multiple sclerosis," Med. Sci. Monit. 2005, vol. 11, pp. BR266-BR373, Medline/NLM Abstract, Accession No. NLM16049372, Abstract only.

(Continued)

*Primary Examiner* — Daniel E Kolker
*Assistant Examiner* — James Rogers
(74) *Attorney, Agent, or Firm* — Shelly Guest Cermak Cermak Nakajima & McGowan LLP

(57) ABSTRACT

A process is provided for the preparation of an immunoglobulin composition from a plasma fraction having immunoglobulins, and antibody preparations prepared utilizing the process.

21 Claims, 1 Drawing Sheet

(56) References Cited

FOREIGN PATENT DOCUMENTS

| WO | WO2005/073252 | 8/2005 |
|---|---|---|
| WO | WO2011/131786 | 10/2011 |

OTHER PUBLICATIONS

Paul, S., et al., "Naturally Occurring Proteolytic Antibodies," J. Biol. Chem. 2004;279(38):39611-39619.
Paul, S., et al., "Antibodies as defensive enzymes," Springer Semin. Immun. 2005;26:485-503.
Planque, S., et al., "Ontogeny of Proteolytic Immunity," J. Biol. Chem. 2004;279(14):14024-14032.
Saveliev, A. N., et al., "Amylolytic activity of IgM and IgG antibodies from patients with multiple sclerosis," Immunol. Lett. 2003;86:291-297.
Search Report for GB Patent App. No. 1006753.6 (Feb. 16, 2011).
International Search Report and Written Opinion for PCT Patent App. No. PCT/EP2011/056486 (Oct. 14, 2011).
Oesser, S., et al., "Protective capacity of a IgM/IgA-enriched polyclonal immunoglobulin-G preparation in endotoxemia," Res. Exp. Med. 1999;198:325-339.
Office Action from co-pending U.S. Appl. No. 13/655,686 dated Jun. 17, 2013.
Mayer, G., Immunology, Chapter 4, Section VI, 2009, The Board of Trustees of the University of South Carolina.
UK IPO Search Report on GB1006753.6 dated Aug. 19, 2010.
Alejandria et al. Intravenous immunoglobulin for treating sepsis, severe sepsis and septic shock. Cochrane Database Syst Rev. 2002, Issue 1. Art. No. CD001090. DOI: 10.1002/14651858.CD001090.
Armstrong et al., Differential expression of Toll-like receptor (TLR)-2 and TLR-4 on monocytes in human sepsis, Clin, Exp. Immunol. 2004; 136:312-319.
Bar-Dayan et al., Neutralization of disease associated autoantibodies by an immunoglobulin M- and immunoglobulin A-enriched human intravenous immunoglobulin preparation, Scand. J. Immunol. 2000; 51(4): 408-414, Abstract.
Bayer Technology Services, "UVivatec® virus inactivation", Product Information, Jan. 2006.
Bryce et al., Who Child Health Epidemiology Reference Group. WHO estimates of the causes of death in children. Lancet. 2005;365:1147-52.
Chetty and Thomson., Management of community acquired pneumonia in children. Pediatr Drugs 9 (6): 401-411, 2007.
Chromogenix S-2288 Product Information, available Dec. 2009.
Cinel et al., Molecular biology of inflammation and sepsis: A primer, Crit. Care Med. 2009; 37(1): 291-304.
Dellinger et al., Surviving Sepsis Campaign: International guidelines for management of severe sepsis and septic shock: 2008, Crit. Care Med. 2008; 36(1): 296-327.
Dremsizov et al., Severe sepsis in community-acquired pneumonia: When does it happen, and do systemic inflammatory response syndrome criteria help predict course? Chest. 2006; 129: 968-978.
Duerr et al., Influence of an Immunoglobulin Enriched (IgG, IgA, IgM) Solution on Activation and Immunomodulatory Functions of Peripheral Blood Mononuclear Cells in Lipopolysaccharide Second Hit Model, Poster presented in Brussels (ISICEM, 22.-25.3.2011).
Duerr et al., Influence of an Immunoglobulin Enriched (IgG, IgA, IgM) Solution on Activation and Immunomodulatory Functions of Peripheral Blood Mononuclear Cells in Lipopolysaccharide Second Hit Model, Abstract presented in Brussels (ISICM, 22.-25.3.2011).
Alejandria et al., Intravenous immunoglobulin for treating sepsis, severe sepsis and septic shock. Cochrane Database Syst Rev. 2010, Issue 1. Art. No. CD001090. DOI: 10.1002/14651858.CD001090.
Durandy A et al. Intravenous immunoglobulins—understanding properties and mechanisms. Clin Exp Immunol. 2009; 158 Suppl 1:2-13.
El-Nawawy, A. et al. Intravenous Polyclonal Immunoglobulin Administration to Sepsis Syndrome Patients: A Prospective Study in a Pediatric Intensive Care Unit. J Trop Pediatr 2005; 51: 271-278.
EMA Guideline on the clinical investigation of human normal immunoglobulin for intravenous administration (IVIg) EMA/CHMP/BPWP/94033/2007 rev 2. Jul. 2010.
EMA Guideline on core SmPC for normal immunoglobulin for intravenous administration (IVIg) 2010 EMA/CHMP/BPWP/94038/2007 rev.3, Oct. 2010.
EMEA ICH Topic S6 Preclinical Safety Evaluation of Biotechnology-Derived Pharmaceuticals (CPMP/ICH/302/95)—Jul. 1997.
EMEA "Note for the Guidance on clinical investigation of human normal immunolgobulin for intravenous administration (IVIg)", CPMP/BPWG/388/95 rev 1, Jun. 2000.
Enk and Knop, Successful management of systemic lupus erythematosus with IgM enriched immunoglobulins, Hautarzt. Jun. 2000; 51(6): 416-8 Abstract.
European Pharmacopoeia 6 (method 2.6.17, Ph. Eur. 6. Edition 2008) in German with English translation.
European Pharmacopoeia 5.0, Test for Fc Function of Immunoglobulin, Method 2.7.9, Jan. 2005.
European Pharmacopoeia 5.0, Immunological Methods, Method 2.7.1, Jan. 2005.
European Pharmacopoeia 7.0, Test for Extractable Volume of Parenteral Preparations, Method 2.9.17, Apr. 2010.
Ewig S, and Torres A. Severe community-acquired pneumonia. Curr Opin Crit Care 8:453-460, 2002.
Fink, M., Presentation Slides "Review of Clinical Trials of anti-TLR4 Agents for Sepsis" From http://www.sepsiscast.com/pdf/Sepsis_SyllabusCAST.pdf, created Jan. 2010.
French, M. (1986) Serum IgG subclasses in normal adults. Monogr. Allergy, vol. 19: 100-107.
Graber & Pfenninger GmbH, Vibrating Mixer Laboratory Type, Product Information www.gandp.ch—available Jun. 2009.
Graber & Pfenninger GmbH, Vibrating Mixer Industrial Type, Product Information www.gandp.ch—available Jun. 2009.
Hellman, J., Presentation Slides "Toll-Like Receptors (TLRs): Focus on the Role of the TLR-Mediated Signaling System in Sepsis" The Science and Medicine of Sepsis Management. From http://www.sepsiscast.com/pdf/Sepsis_SyllabusCAST.pdf, created Jan. 2010.
Huang et al., Community-acquired pneumonia in Shanghai, China: microbial etiology and implications for empirical therapy in a prospective study of 389 patients. Eur J Clin Microbiol Infect Dis. 2006;25:369-74.
IBL Gesellschaft Fur Immunchemie und Immunbiologie MBH "C5a ELISA RE59292 Instructions for Use", May 2004.
ICH Preclinical safety evaluation of biotechnology-derived pharmaceuticals S6(R1), Addendum, Jun. 2011.
ICH Guidelines on Nonclinical Safety Studies for the Conduct of Human Clinical Trials and Marketing Authorisations for Pharmaceuticals, M3(R2), Jun. 2009.
ICH Specification: Test Procedures and Acceptance Criteria for Biotechnological/Biological Products, Q6B, Mar. 1999.
Jacobs et al., Effect of pentaglobin and pipeacillin on survival in a rat model of faecal peritonitis: importance of intervention timings, Acta Anaesthesiologica Scand. Jan. 2000;44(1):88-95 Abstract.
Jokinen et al. Incidence of community-acquired pneumonia in the population of four municipalities in Eastern Finland. Am J Epidemiol. 1993;137:977-88.
Kamiya Biomedical Company "Rabbit Complement 3(C3) ELISA Kit, MBS701356" Package Insert, Feb. 2009.
Koch and Zacharowski, Toll-like receptor pathway signalling is differently regulated in neutrophils and peripheral mononuclear cells of patients with sepsis, severe sepsis, and septic shock, Crit. Care Med. 2009, 37(1): 346-347.
Kreymann et al., Use of polyclonal immunoglobulins as adjunctive therapy for sepsis or septic shock. Crit Care Med. 2007;35:2677-2685.
Lim et al., Defining community acquired pneumonia severity on presentation to hospital: an international derivation and validation study. Thorax 2003;58:377-382.
Lim et al., Pneumonia Guidelines Committee of the BTS Standards of Care Committee. BTS guidelines for the management of community acquired pneumonia in adults: update 2009. Thorax. 2010;64 Suppl 3:iii1-55.

(56) References Cited

OTHER PUBLICATIONS

Mandell et al., Infectious Diseases Society of America/American Thoracic Society Consensus Guidelines on the Management of Community-Acquired Pneumonia in Adults. Clin Infect Dis. 2007;44: S27-72.
Marggraf, G. et al Ergebnis einer mulitzentrischen randomisierten und kontrollierten Studie mit Pentaglobin zur adjuvanten Therapie der Mediastinitis, Intensivmedizin und Notfallmedizin, Band 41, Heft 4 (2004): 272 and EN translation thereof.
Marshall and Reinhart, Biomarkers of sepsis, Crit. Care Med. 2009; 37(7): 2290-2298.
Marshak-Rothstein, A., Toll-like receptors in systemic autoimmune disease, Nat. Rev. Immuno. 2006; 6(11) : 823-35, Abstract.
Mayer G., "Immunoglobulins—Structure and Function", Immunology, Chapter IV, online publication. Copyright 2009, The Board of Trustees of the University of South Carolina.
McIntosh K. Community-acquired pneumonia in children. N Engl J Med. 2002;346:429-37.
Miletic et al., Regulation of complement activity by immunoglobulin. 1. Effect of immunoglobulin isotype on C4 uptake on antibody-sensitised sheep erythrocytes and solid phase immune complexes. J. Immunol. 1996, 156(2): 749-757.
Miller et al., Ensuring the pathogen safety of intravenous immunoglobulin and other human plasma-derived therapeutic proteins, J Allergy Clin. Immunol. 2001; 108: S91-4.
Moine et al., Severe community-acquired pneumonia. Etiology, epidemiology, and prognosis factors. French Study Group for Community-Acquired Pneumonia in the Intensive Care Unit. Chest. 1994;105:1487-95.
Ng et al. "Process-scale purification of immunoglobulin M concentrate" Vox Sang, vol. 65, pp. 81-86 (1993).
Oosterheert et al., Severe community-acquired pneumonia: what's in a name? Curr Opin Infect Dis. 2003;16:153-9.
Ostapchuk et al., Community-Acquired Pneumonia in Infants and Children. Am Fam Physician 70:899-908, 2004.
Perosa et al. "Purification of human immunoglobulins by sequential precipitation with caprylic acid and ammonium sulfate." J Immunol Methods, vol. 128, pp. 9-16 (1990).
Pertierra et al., "Fundamentos de Bioqulmica" (Fundamentals of Biochemistry)2nd Edition, Published by Tébar, 2006, p. 115.
Quidel MicroVue C5a EIA Kit Product Information, Dec. 2009.
Quidel MicroVue C3a EIA Kit Product Information, Feb. 2011.
Reiben et al., Immunoglobulin M-enriched human intravenous immunoglobulin prevents complement activation in vitro and in vivo in a rat model of acute inflammation. Blood, 1999, 93(3), 942-951.
Reinhart et al., Extract and EN translation of section bridging pp. 36 and 37 of Prävention, Diagnose, Therapie and Nachsorge der Sepsis, (Revision of S-2K Guidelines of the German Sepsis Society eV(DSG) and the German Interdisciplinary Association for Intensive and Emergency Medicine (DIVI), approved Feb. 2010.
Reith et al., IgM-enriched immunoglobulin (Pentaglobin) poitively influences the course of post-surgical intra-abdominal infections. Eur J Med Res 2004; 9: 1-6.
Rittirsch et al, Harmful molecular mechanisms in sepsis, Nature Reviews Immunology, 2008; 8: 776-787.
Roger et al., Protection from lethal Gram-negative bacterial sepsis by targeting Toll-like receptor 4, PNAS 2009; 106 (7): 2348-2352.
Rodríguez, A. et al. Effects of high-dose of intravenous immunoglobulin and antibiotics on survival for severe sepsis undergoing surgery. Shock 2005; 23: 298-304.
Rütten Engineering AG, Vibrating Agitators, (available: Jun. 2009 www.rutten.com/Vibrating%20Agitators_e.htm).
Schoenfeld DA and Bernard GR Statistical evaluation of ventilator-free days as an efficacy measure in clinical trials of treatments for acute resoiratory distress syndrome. Crit Care Med. 2002;30:1772-1777.
Tidswell et al., Phase 2 trial of eritoran tetrasodium (E5564), a Toll-like receptor 4 antagonist, in patients with severe sepsis Crit. Care Med. 2010; 38(1): 72-83.
Torres et al., Severe community-acquired pneumonia. Epidemiology and prognostic factors. Am Rev Respir Dis. 1991;144:312-8.
Trotter et al., Increasing hospital admissions for pneumonia, England. Emerg Infect Dis. 2008;14:727-33.
Tsujimoto et al., Role of Toll-like receptors in the development of Sepsis, Shock, 2008; 29(3): 315-321.
US Code of Federal Regulations 21, (Immunoglobulin Preparations) 21 CFR 640.104, Apr. 2010.
van der Poll and Opal, Host-pathogen interactions in sepsis, The Lancet, 2008; 8: 32-43.
Vassilev et al., IgM enriched human intravenous immunoglobulin suppresses T lymphocyte functions in vitro and delays the activation of T lymphocytes in hu-SCID mice, Clin. Exp. Immunol. 2006; 145: 108-115.
Virkki et al., Differentiation of bacterial and viral pneumonia in children. Thorax. 2002;57:438-41.
Weigl et al., Population-based incidence of severe pneumonia in children in Kiel, Germany. Klin Padiatr. 2005;217:211-9.
Wickerhauser et al., "Large scale preparation of macroglobulin", Vox Sang, 23, 119-125 (1972).
Williams et al., Modulation of tissue Toll-like receptor 2 and 4 during the early phases of polymicrobial sepsis correlates with mortality, Crit. Care Med. 2003; 31(6): 1808-1818.
Woodhead M. Community-acquired pneumonia in Europe: causative pathogens and resistance patterns. Eur Respir J 20 (Suppl. 36): 20s-27s, 2002.
Woodhead et al., Community-acquired pneumonia on the intensive care unit: secondary analysis of 17,869 cases in the ICNARC Case Mix Programme Database. Crit Care. 2006;10 Suppl 2:S1.
Zhang M et al. Activation of the Lectin Pathway by Natural IgM in a Model of Ischemia/Repurfusion Injury. J Immunol. 2006; 1:177:4727-34.
Janeway et al., (2005) Immunobiology, 6th Edition, p. 156.
Fachinformation (Zusammenfassung Der Merkmale Des Arzneimittels/SPC) and EN translation thereof, Jul. 2010.
Höffken G. et al. Extract and EN translation of part of pp. e14-e15 of S3-Leitlinie zu ambulant erworbener Pneumonie und tiefen Atemwegsinfektionen (S3-guidelines on Ambulant Acquired Pneumonia and Deep Airway Infections, Pneumonie 2005; 59: e1-e63.
Höffken G. et al. Extract and EN translation of part of pp. e14-e15 of Epidemiologie, Diagnostik, antimikrobielle Therapie und Managementvon erwachsenen Patienten mit ambulant unteren Atemwegsinfektionen sowie ambulant erworbener Pneumonie—Update 2009, Pneumologie 2009; 63: e1-e68.
Jarvis, J. N., et al., "Composition and biological behaviour of immune complexes isolated from synovial fluid of patients with juvenile rheumatoid arthritis," Clin. Exp. Immunol. 1995;100:514-518.
Official Action for Russian App. No. 2012149743 (Feb. 3, 2015) with English language translation thereof.
Playfair, J. H. L., Excerpt from Immunology At a Glance, Fifth Edition, Blackwell Scientific Publications, 1992, p. 16.
Roitt, I., et al., Excerpt from Immunology, Third Edition, 1993, Mosby-Year Book Europe Limited, pp. 44-45.
International Search Report for PCT Patent App. No. PCT/EP2011/056487 (Oct. 17, 2011).
International Preliminary Report on Patentability for PCT Patent App. No. PCT/EP2011/056487 (Oct. 23, 2012).
International Preliminary Report on Patentability for PCT Patent App. No. PCT/EP2011/056486 (Oct. 23, 2012).

* cited by examiner

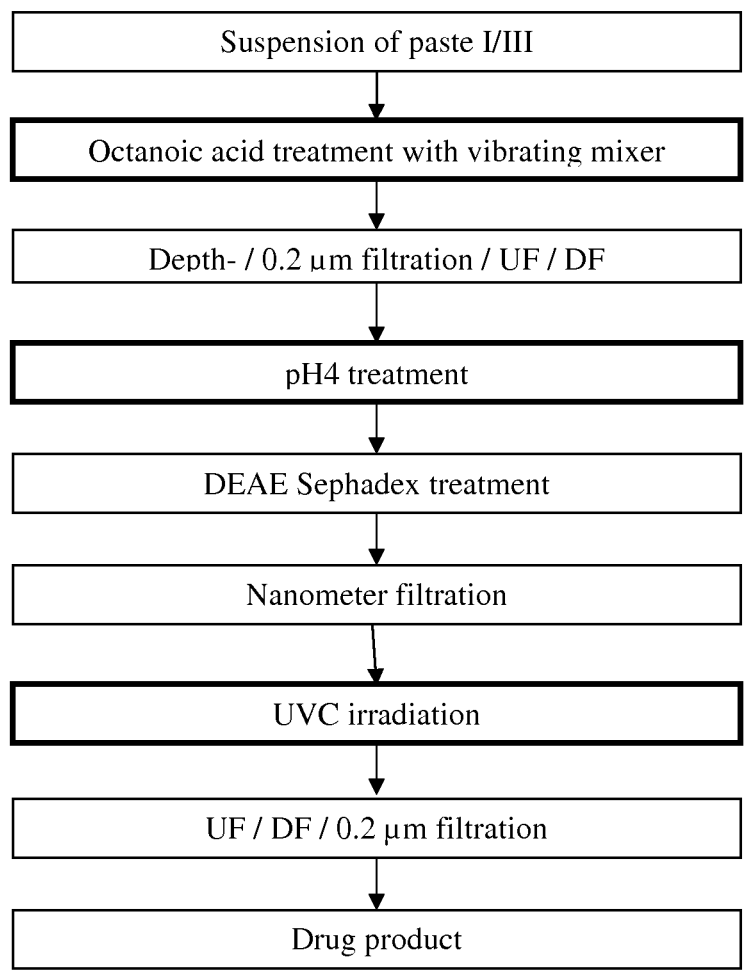

PROCESS FOR PREPARING AN IMMUNOGLOBULIN COMPOSITION

This application is a Continuation of, and claims priority under 35 U.S.C. §120 to, International Application No. PCT/EP2011/056486, filed Apr. 21, 2011, and claims priority therethrough under 35 U.S.C. §119 to Great Britain Patent Application No. 1006753.6, filed Apr. 22, 2010, the entireties of which are incorporated by reference herein.

FIELD OF THE INVENTION

The present invention relates to a process for the preparation of a virus safe immunoglobulin composition, and antibody preparations and pharmaceutical compositions which can be prepared using the process.

BACKGROUND OF THE INVENTION

Immunoglobulin compositions prepared from human plasma and suitable for intravenous administration are known in the art and for several decades have played an important role in the treatment of a wide range of diseases. Immunoglobulins are used, for example, for the treatment of infections in humans and can be assigned to various classes with various biochemical and physiological properties. Immunoglobulin G participates in defending against viral antigens, whereas IgM is predominantly active in antibacterial and antitoxin immune responses.

The immunoglobulin solutions comprise IgG, IgA and IgM in various percentages, with different preparations having different treatment applications, e.g. preparations with a higher percentage of IgM are used in the prophylaxis or treatment of bacterial infections. In contrast to IgG preparations IgM antibodies easily aggregate in solution. IgM preparations are difficult to stabilize especially if they are enriched compared to plasma concentrations and stored in liquid solution.

The immunoglobulin solutions are usually prepared from fractions of blood plasma or serum, e.g. Cohn fractions. These fractions are then subjected to a number of purification steps to remove contaminants including viruses, denatured proteins, proteases and lipids. Human plasma for fractionation is collected from thousands of donors and may contain pathogen viruses despite thorough testing of the source plasma. Therefore process steps to inactivate or remove viruses are essential in order to achieve safe products for use in medicine. Several techniques for virus inactivation/removal are known in the art, e.g. chemical treatments, irradiation with UVC light or nanometer filtration, which are performed in order to ensure overall virus safety. However, such steps can have a negative impact on the activity of the immunoglobulins; for example extended irradiation times with UVC can reduce the yield of native and active IgM obtained in the final immunoglobulin solution.

The virus removal or inactivation capacity of the process steps is validated using laboratory scale models of the production process and for each step a removal or inactivation factor is determined. An increase of the inactivation/removal factor adds additional viral safety to the pharmaceutical product. Today guidelines from regulatory authorities require at least two effective steps for enveloped and non-enveloped viruses in the manufacture of plasma-derived pharmaceuticals.

In addition to viruses which are potentially present it is also necessary to remove other contaminants like proteases, protein aggregates, and denatured immunoglobulins, to achieve a well tolerated product. Denatured immunoglobulins especially are a potential risk for the patients because they have a high capacity to activate complement unspecifically, leading to severe side effects in patients receiving these denatured immunoglobulins. This anticomplementary activity (ACA) is measured by a standardized test described in the European Pharmacopoeia.

The removal of all these contaminants is essential (1) in order for the product to be tolerated by the patient after intravenous administration, (2) to ensure the product complies with bio-safety guidelines regarding viral contamination, (3) to allow the product to be stable during long-term storage, and (4) to generate the desired compound mixture/pharmaceutical composition.

The initial purification of human IgM solutions has been carried out by classical Cohn plasma fractionation methods or its well known modifications (e.g. Cohn/Oncley, Kistler/Nitschmann). Using cold ethanol precipitation processes the IgM fraction is recovered in fraction III or fraction I/III (also called B or B+I). Starting from fraction III or I/III methods have been described for purification of protein solutions enriched in IgM. EP0013901 describes a purification method starting from fraction III including steps using octanoic acid, β-Propiolactone and an adsorption step using an anionic exchange resin. This method is used to produce Pentaglobin®—to date the only commercially available intravenous IgM product. EP0352500 describes the preparation of an IgM concentrate for intravenous application with a reduced anti-complementary activity by using anionic exchange chromatography, β-Propiolactone, UVC light irradiation and an incubation step at increased temperature (40° C. to 60° C.). β-propiolactone is a well known chemical used in sterilization steps in order to inactivate viruses which are potentially present. As β-propiolactone is a very reactive substance which causes the chemical modification of proteins there is also substantial loss of the anti-viral and anti-bacterial activities of the immunoglobulins. The preparation produced by this method was stable in liquid solution for a limited time due to the chemical modification. The IgM concentration was above 50% from the total immunoglobulin content.

The preparation of protein solutions enriched in IgM without chemical modification by β-propiolactone has been described in EP0413187 (Biotest) and EP0413188 (Biotest). These methods involve subjecting a suitable protein solution to octanoic acid treatment and anionic exchange chromatography, starting from Cohn fraction III or II/III. In patent EP0413187 (Biotest) the octanoic acid treatment is carried out by stirring for 15 min, in order to remove lipids being present in Cohn fraction III.

As large amounts of immunoglobulins are administered intravenously to patients a tolerable pharmaceutical preparation must be achieved. IgM preparations have been described as being difficult to prepare for intravenous application. IgM by nature is a vigorous activator of complement after the binding of antigens. Therefore unspecific anticomplementary activity of denatured IgM molecules is far more dangerous to patients than denatured IgG molecules. The preparation according to EP0413187 had a low anticomplementary activity, between 0.6 and 0.8 CH50/mg protein, but had to be stabilized and virus inactivated by β-propiolactone. Low anticomplementary activity is considered to be ≤1 CH50/mg protein according to EP monograph for immunoglobulins.

EP0413188B1 (Biotest) describes the preparation of an IgM-enriched preparation for intravenous administration by using an anion exchange chromatography in order to reduce the anti-complementary activity. Additionally a heat treatment at pH 4-4.5 at 40 to 60° C., preferably between 50 and 54° C., was described to reduce the anticomplementary activity. This preparation had to be lyophilized to ensure stability of the preparation for several months. Long term stability as a liquid solution could not be shown.

Another method describes the use of mild-heat treatment of IgM preparations at 40 to 62° C., preferably 45 to 55° C., at pH 4.0 to 5.0 (EP 0450412, Miles) to reduce the non-specific complement activation. In this patent application octanoic acid is added to a Cohn fraction III suspension in order to remove prekallikrein activator and lipoproteins by centrifugation. Nevertheless this treatment led to partial loss of antigenic determinants of IgM. This may increase the risk of generating neo-antigens leading to a increased immunogenicity in humans or the loss of activity.

The preparation of an IgM containing protein solution for intravenous application by using a protease treatment (e.g. with pepsin) after an octanoic acid precipitation step has been described in EP0835880 (U.S. Pat. No. 6,136,312, ZLB). Protease treatment leads to partial fragmentation of the immunoglobulin molecule impairing the full functional activity of the Fab and Fc parts. Therefore protease-treated immunoglobulins cannot be regarded as unmodified. Also this preparation method leads to about 5% fragments with a molecular weight of <100 kD.

The described methods to carry out the octanoic acid treatment (EP0413187 and EP0835880) have the drawback that the octanoic acid treatment is not effective with respect to removal and inactivation of non-enveloped viruses, and does not remove substantially all proteolytic activity.

In EP 0345543 (Bayer, Miles) a highly concentrated IgM preparation with at least 33% IgM for therapeutic use is disclosed, the preparation being substantially free of isoagglutinin titres. In this patent application an octanoic acid precipitation is carried out by adding the octanoic acid and the isoagglutinins are removed by Synsorb affinity chromatography. The final preparation had to be freeze dried.

Altogether the preparation of a IgM containing preparation with low anticomplementary activity is possible if the immunoglobulins are chemically or enzymatically modified and/or further purified by chromatography and/or subjected to a mild heat treatment.

Nevertheless the methods of the prior art leading to an unmodified immunoglobulin preparation are not able to achieve the virus inactivation capacity for all viruses which are potentially present. Although several methods, such as solvent/detergent treatment, octanoic acid treatment, nanometer filtration and heat treatment, are effective to inactivate or remove enveloped viruses there are only a few methods known to inactivate or remove non-enveloped viruses, for example Parvo viruses. These non-enveloped viruses are mostly very small, usually passing through nanometer filters with pore sizes above 20 nm. This pore size is too small for IgM molecules having a diameter up to 30 nm. Non enveloped viruses are effectively inactivated by chemicals like β-propiolactone which, however, also leads to a modified immunoglobulin with impaired functions. Another effective treatment is UVC-irradiation (EP1842561, CAF-DCF). However, known solvent/detergent treatments, octanoic acid treatment and mild heat treatment have no substantial effect on non-enveloped viruses.

Therefore all the chemically unmodified IgM containing preparations, which are prepared by the methods of the prior art, and which have low anticomplementary activity, are not safe for human use with respect to non enveloped viruses e.g. Parvoviruses.

In summary the methods of the prior art which isolate an intravenous-tolerable IgM-containing preparations have certain drawbacks, such as an inability to effectively inactivate or remove non-enveloped viruses and the limited ability to remove proteolytic activity while keeping IgM with high yield in solution. (Proteolytic activity refers to the sum of proteases being present in the preparation). As a liquid protein preparation must be storable for long periods (e.g. 2 years), residual protease activities must be omitted, as these activities might lead to degradation of the pharmaceutical preparation.

Thus, it is the aim of the present invention to address these drawbacks.

SUMMARY

In a first aspect the present invention provides a process for the preparation of an IgM immunoglobulin composition from a plasma fraction comprising immunoglobulins, the process comprising:
(a) providing a plasma fraction as a solution containing the immunoglobulins;
(b) mixing a $C_7$ to $C_9$ carboxylic acid with the solution and treating the mixed solution with a vibrating agitator to precipitate contaminating proteins; and
(c) separating the precipitated proteins from the solution to yield the IgM containing immunoglobulin composition.

The present applicants have surprisingly found that the use of a vibrating agitator during the step where the immunoglobulin solution is mixed with the carboxylic acid is extremely advantageous. This method step provides a more efficient removal of unwanted proteins (including proteases) and produces an intermediate product which is better suited to downstream processing steps utilised to produce an immunoglobulin medicament; the intermediate product allows these downstream processing steps to be more efficient. In particular, the IgM immunoglobulin containing composition obtained from step (c) can be combined with further treatment steps, such as treatment with mild acid conditions and treatment with UVC irradiation, to produce an IgM containing immunoglobulin product or antibody preparation which is suitable for intravenous administration and which has the following advantageous properties: (i) being chemically unmodified; (ii) being virus safe (iii) having low proteolytic activity (and therefore being stable during long term storage); (iv) having low anti-complementary activity; and (v) retaining a high level of native and active IgM. The level of virus safety achieved with the methods described herein has not previously been obtaininable. Further, the use of the method of the present invention achieves an IgM containing immunoglobulin product or antibody preparation with combinations of these features which have not previously been obtainable.

In particular, the method steps of the present invention lead to a higher inactivation and removal of virus particles, especially very resistant, non-enveloped viruses such as Parvo viruses, which are usually not very susceptible to octanoic acid treatment. Furthermore, an improved removal of proteolytic activity is achieved in comparison to conventional stirring. These features are achieved while keeping a high yield of IgM that is chemically unmodified. This finding contrasts with the conventional view that the treatment with octanoic acid is not an effective step against non-enveloped viruses and improved viral safety must be achieved through inactivation of virus through harsher methods such as β-Propiolactone treatment. Also it was well known that increasing e.g. octanoic acid concentration to completely remove proteolytic activity results in a massive loss of IgM.

The results of the present invention are achieved through the use of mixing devices using a vibrating mode in combination with the octanoic acid treatment. This is particularly surprising since it is known that IgM is very susceptible to shear stress, which may lead to an undesired high anticomplementary activity. Accordingly, one would not consider using a vibrating mixer to prepare an IgM composition and would not expect such a favorable impact when using a vibrating mixing during processing of an IgM containing solution.

Furthermore with the method of the present invention the separation achieved by step (c), such as clarification by filtration of the octanoic acid treated solution resulting from step (b), is enhanced when a vibrating mixing device is used. Separation is more easily achieved, reducing processing time and manufacturing costs, and step (c) leads to a limpid solution which creates advantages for downstream processing. Conventional solutions, achieved by filtering the results of octanoic acid treated IgM containing solutions which have been stirred, are opalescent or opaque.

The resulting IgM containing composition obtained from step (c) is preferably subjected to treatment with mild acid conditions (e.g. pH 4) and an UVC-irradiation step to further improve virus safety and stabilize the final product. Due to the enhanced clarification of the IgM containing immunoglobulin composition obtained from step (c) it is possible to lower the necessary irradiation time with UVC to achieve a virus inactivation of non enveloped viruses of more than 3 or 4 $\log_{10}$. This results in a higher yield of native and active IgM during UVC treatment.

Surprisingly these steps lead to a chemically and enzymatically unmodified IgM containing solution which has higher yields of native and active IgM, having low anticomplementary activity and low proteolytic activity and having high antibacterial and antiviral activity, with an outstanding virus safety concerning enveloped and non enveloped viruses; a key feature for pharmaceuticals which are for intravenous administration. Moreover, a treated IgM containing solution has improved long term stability being very stable in liquid solution for more than 12 months at 2-8° C.

Accordingly, in a further aspect the present invention provides an antibody preparation obtainable using the process of the present invention set out above and an antibody preparation comprising IgM and having a proteolytic activity of less than 8 U/l. In particular, the antibody preparation is suitable for intravenous administration in humans and comprises IgG, IgA and IgM, wherein at least 5% of the total immunoglobulins are IgM.

Still further, the present invention provides an antibody preparation of the present invention for use in medicine. In one embodiment the antibody preparation is for use in the treatment of immunological disorders and bacterial infections.

A further aspect of the present invention provides a method of treatment comprising administering the antibody preparation of the present invention to a patient.

The present invention will now be described in further detail by way of example only, with reference to the accompanying figures.

FIG. 1 provides an overview of an embodiment of the invention in which the steps that can be utilised to form an antibody preparation suitable for intravenous admininstration are shown. The octanoic acid treatment step employing a vibromixer device, the pH4 treatment and the UVC treatment are highlighted. The starting material is generated from a standard cold ethanol precipitation process of human plasma.

DETAILED DESCRIPTION OF EXEMPLARY EMBODIMENTS

As described above, the present invention provides a process for the preparation of an IgM containing immunoglobulin composition from a plasma fraction comprising immunoglobulins. Plasma fractions suitable for the preparation of pharmaceutical immunoglobulin compositions, and methods for their production are well known in the art. In particular, where the pharmaceutical immunoglobulin compositions are for administration to humans, the plasma fraction is obtained from human plasma. The plasma fraction is preferably a precipitated plasma fraction and most preferably a precipitated plasma fraction obtained by the process of Cohn fractionation or its well known modifications (e.g. Kistler-Nitschmann). Most preferably the fraction is fraction I/III or fraction III (also known as fraction B+I or fraction B) out of cold ethanol fractionation. It is preferred that the immunoglobulins of the plasma fraction comprise at least 5% IgM.

Step (a) comprises providing a plasma fraction as a solution containing the immunoglobulins. In many cases the plasma fraction containing the immunoglobulins will be in solid or semi-solid form. Thus the aim of this step is to ensure or to bring the protein of the plasma fraction into solution such that it is in a suitable state for mixing with the carboxylic acid in step (b). This step may comprise mixing the plasma fraction with a suitable buffer. Preferably the buffer is of low molarity (i.e. less than 1M) and has a pH between 4.5 and 5.5 e.g. 0.1 M sodium acetate buffer pH 5.05±0.1. Mixing can be completed using a blade mixer or a vibrating agitator.

In step (b) the solution formed in step (a) is mixed using a vibrating agitator with a $C_7$ to $C_9$ carboxylic acid to precipitate contaminating proteins (e.g. proteases, viruses etc). The carboxylic acid may be branched and/or may include substituents which do not substantially alter the effect of step (b). The carboxylic acid is preferably octanoic acid. The acid is preferably added at a concentration of at least 0.075 kg/kg of plasma fraction, up to a concentration of 0.2 kg/kg. More preferably the acid is added at 0.8 to 0.15 kg/kg of plasma fraction, and most preferably between 0.09 kg/kg and 0.13 kg/kg. Acid of any convenient molarity may be used to provide the correct concentration.

Any type of commercially available vibrating agitator, suitable for use in the chemical/pharmaceutical industry, may be used. Examples of suitable vibrating agitators are available from Graber+Pfenninger GmbH. In particular, the "Labormodell Typ 1" vibromixer can be used for lab scale experiments, and the "Industriemixer Typ 4" can be used for production scale preparations. The vibrating mixers can be used according to manufacturer's instructions, and in particular at settings which are described by the manufacturers as suitable for mixing solutions containing proteins. For example the vibrating mixers can usually be operated at less than 100 Hz with an amplitude less than 10 mm, e.g. the vibration mixing using the "Labormodell Typ 1" at lab scale was carried out by the present inventors at 50 Hz, when 230 V power supply is used. The vibration amplitude of the mixing process was varied between 0 and 3 mm, and for the IgM preparation preferably 3 mm was used. Stirrer plates with a diameter between 23 mm and 65 mm were used for lab scale experiments. For production scale a stirrer plate diameter of 395 mm was used (hole diameters of 13.5 mm and 16 mm).

In step (b) the pH of the mixed solution is preferably between 4.5 to 5.5, and more preferably between pH 4.8 and pH 5.3. The step can be carried out in sodium acetate buffer, and, for example, with approximately 0.1 M sodium acetate buffer. The temperature at which step (b) is conducted is preferably between 10° C. and 35° C., and more preferably 14 to 30° C.

The mixing time using the vibrating agitator is not particularly limited but is preferably at least 30 minutes and not more than 3 hours, and more preferably from 40-110 minutes. Incubation times of less than 30 minutes can reduce the level of virus inactivation.

In one embodiment of step (b) tri-calcium phosphate is mixed with the solution in step (b). Preferably this is added at 0.01 to 0.02 kg/kg plasma fraction (as it is in solid or semi-solid form). The tri-calcium phosphate can be added simultaneously, separately or sequentially to the carboxylic acid. In a preferred embodiment the tri-calcium phosphate is added at least 20 minutes after the carboxylic acid.

In step (c) the contaminating proteins precipitated in step (b) are separated off from the solution to yield the IgM containing immunoglobulin composition (i.e. an immunoglobulin containing solution). This step of separation is not particularly limited but can be performed by any suitable method known in the art. However, the separating step is preferably performed using filtration, and more preferably ultrafiltration, and the result of step (c) is therefore a filtered solution.

As described above, the method of the present invention is advantageous in manufacturing terms since it appears to cause a more efficient precipitation of contaminating proteins, and, as a result, step (c) is easier to perform. When the mixture resulting from step (b) is separated, a transparently clear solution, i.e. the IgM containing immunoglobulin composition, is achieved. Filtration is is therefore quicker and easier.

Further process steps are required to convert the IgM containing immunoglobulin composition obtained from step (c) into an immunoglobulin preparation suitable for intravenous administration.

Accordingly, in a preferred embodiment the process of the present invention comprises the additional steps of treating the IgM containing immunoglobulin composition obtained from step (c) with mild acid conditions and, further, subjecting the acid treated composition to UVC irradiation.

For the treatment with mild acid conditions the IgM containing immunoglobulin composition obtained from step (c) is incubated at between pH 3.5 to pH 4.5, and preferably between pH3.8 and pH4.2, to form an incubated solution. The mild acid conditions can be created by adding a suitable acid to the IgM containing immunoglobulin composition, for example the pH can be adjusted by adding 0.2M HCl.

This incubation step is preferably carried out at between 32 and 42° C., and more preferably at between 35 and 39° C. The incubation time is preferably at least 2 hours and not greater than 24 hours, and more preferably at least 9 hours but not greater than 16 hours.

In the irradiation step the incubated solution obtained from the mild acid treatment described above is treated with UVC light to form a UVC irradiated solution. This step can be performed using devices which are commercially available, such as the UVivatec® device (Bayer Technology Services). It is preferred that the incubated solution is treated at 254±10 nm between 200 and 500 J/m$^2$, more particularly between 200 and 300 J/m$^2$, in order to further inactivate viruses and proteases which are potentially present. It is noted that UVC treatment under gentle conditions than would normally be required is only possible with the water-clear filtrate which is obtained by the present invention after the octanoic acid treatment with vibromixing. More opalescent or opaque solutions normally received by standard stifling techniques would necessitate longer irradiation times which would lead to more denaturation of the IgM activity and lower virus inactivation rates.

In addition to the mild acid treatment and the UVC irradiation the additional steps to achieve an immunoglobulin preparation for intravenous administration can optionally also comprise one or more filtration steps. In one embodiment the protein solution being processed can be adsorbed onto DEAE-Sephadex and then separated from the Sephadex by depth filtration. For example, it may further be subjected to a batch adsorption with 75 mg per kg protein DEAE Sephadex at pH 5.8, in order to remove the unwanted accompanying protein Ceruloplasmin.

In a particularly preferred embodiment the incubated solution obtained from the mild acid treatment is subjected to adsorption onto DEAE-Sephadex and then separated from the Sephadex by depth filtration, before being treated to UVC irradiation.

In another embodiment the immunoglobulin solution being processed may be filtered through a nanometer filter. Filters of 75±5 nm to 35±5 nm pore size, or filters having a nominal pore size of 75 to 35 nm (for example Pall Ultipor DV50), can be used at various stages during the process. (A nominal pore size of e.g. 50 nm means retention rate of ≥4 log 10 for virus with size of 50 nm or larger). In a preferred embodiment the solution obtained from the DEAE-Sephadex step described in the above paragraph is filtered through a 0.2 µm filter prior to UVC irradiation. In a further preferred embodiment the immunoglobulin solution obtained after UVC irradiation is subjected to nanofiltration, preferably through a filter having a 40 to 50 nm pore size. It is preferred that this step should be carried out under sterile conditions.

The final antibody preparation (i.e. the processed IgM containing immunoglobulin solution) obtained from the process defined above may be directly filled into a container under sterile conditions. Alternatively, the antibody preparation may be formulated with a stabilizing agent, such as glycine. In particular, the preparation may be formulated in a glycine-containing buffer at a pH between 4 and 5.5, and preferably between 4.1 to 4.5. The antibody preparation may also be diluted to a protein concentration between 40 and 80 g/L and preferably between 55 and 70 g/L.

Preferably the process of the present invention does not comprise a step involving one or more of chemical modification of the antibodies in the preparation, enzymatic modification of the antibodies, or heat treatment of the antibodies (e.g. treatment of the antibodies at a temperature of 40° C. or more for 10 minutes or more). More particularly the process of the present invention does not include a step of contacting the antibodies with β-propiolactone and/or pepsin.

The present invention further provides an immunoglobulin preparation or antibody preparation obtainable by the process described above. The immunoglobulin preparation is polyclonal and can comprise at least 5% IgM, preferably at least 15% IgM and most preferably at least 20% IgM. The other immunoglobulins are IgG and IgA. Preferably the immunoglobulin preparation comprises between 5 and 30% IgM (most preferably between about 15 and 30%), between 5 and 30% IgA (most preferably between 15 and 30%) and between 40 and 70% IgG (most preferably between 45 and 70%). In the most preferred product the IgG content is about 50% and the IgM and IgA content each are about 25%. The values mean the percentage of e.g. IgM from the sum of IgG+IgA+IgM. Nevertheless it is also possible to enrich the IgM further by well known methods like e.g. anion exchange chromatography. The values can be determined by nephelometry or by immunoprecipitation according Ph. Eur. (current edition (2010) 2.9.17).

In particular, the immunoglobulins in the immunoglobulin preparation are not chemically modified. The immunoglobulin preparation has not been treated during its process of production with a chemical such as β-propiolactone to sterilize the product. Similarly the preparation has not been treated with an added protease, such as pepsin, to sterilize the product. As such, the immunoglobulins are substantially in native form.

The antibody preparation has a lower proteolytic activity than the antibody preparations described in the prior art. In particular, no proteolytic activity is detectable in the preparation when it is stored at between 2 to 8° C. The proteolytic activity can be measured by standardized test methods known in the art, such as that using the chromogenic substrate which is described below in example 6. In such methods proteolytic activity is assessed by mixing a chromogenic substrate (in particular those sensitive to at least one serine protease) and a sample of the antibody preparation (usually diluted in buffer to meet the linear range of the assay) at 37° C. and monitoring the absorption kinetics using a spectrophotometer. The proteolytic activity of the sample is calculated from the initial absorption difference ($\Delta$Abs/min) by using the equation C (U/L)=S×$\Delta$Abs/min×F (C=proteolytic activity; S=conversion factor relating to specific adsorption change of the chromogenic substrate; and F=dilution factor). Use of the substrate is according to manufacturer's instructions.

The proteolytic activity can in particular be assessed via the following steps:
(a) 25 mg of the substrate S-2288 (Chromogenix) is dissolved in 7.2 ml of water-for-injection;
(b) a sample of the antibody preparation is diluted into buffer (100 mM Tris.HCl pH 8.4, 106 mM NaCl) to meet the linear range of the assay and temperature is adjusted to 37° C.;
(c) equal amounts (e.g. 200 µl) of the diluted antibody preparation and the dissolved substrate are mixed;
(d) the absorption kinetics are measured at 405 nm for 1 to 3 minutes at 37° C. using a spectrophotometer;
(e) the proteolytic activity of the sample is calculated from the initial absorption difference ($\Delta$Abs/min) by using the equation C (U/L)=313×$\Delta$Abs/min×F (C=proteolytic activity, F=dilution factor)

The limit of quantitation of this method is 8 U/l, and using a sample of the antibody preparation of the present invention proteolytic activity is undetectable. As such the level of the proteolytic activity in the final product of the present invention is below 8 U/l.

As with preparations known in the art the antibody preparation of the present invention can be stored at 5±3° C. However, due to the efficient purification with the method of the present invention the stability of the antibody preparation is extremely good. The final product is stable in liquid form for at least 3 months, preferably at least 6 months and most preferably at least two years at 2 to 8° C., which means that there is no fragmentation or polymerization of IgM above 5% measured in HPSEC, no increase of proteolytic activity, no decrease of IgM antibody activity against Escherichia coli and IgM antibody activity against Pneumococcus saccharide of more than 25% and no increase in anticomplementary activity of more than 25%, staying below 1 CH50/mg protein. Still further, the final product produced by the method of the present invention is stable in liquid form for at least 3 months, preferably at least 6 months, and most preferably at least one year at room temperature (between 23 and 27° C.) as assessed by the same criteria.

The process of the present invention further provides a higher level of virus removal than the processes of the prior art resulting in an antibody preparation which is safer than the antibody preparations of the prior art, particularly with respect to active non enveloped viruses like, for example, parvoviruses. The method of the present invention is capable of removing/inactivating viruses, and in particular non-enveloped virus, by more than 3 $\log_{10}$, preferably by more than 4 $\log_{10}$, and most preferably by more than 5 $\log_{10}$. This results in an antibody preparation that is substantially free of virus, and in particular substantially free of non-enveloped virus (i.e. is virus-safe). Still further, the method of the present invention is able to achieve this level of viral particle removal/inactivation without a significant impact on the amount of active IgM or on the anticomplementary activity of the antibody preparation. Accordingly, antibody preparations which are virus safe with respect to enveloped and non-enveloped virus, which contain at least 15%, more preferably at least 20% level of IgM and which have anticomplementary activity of ≤1 CH 50/mg protein are obtainable.

The antibody preparation of the present invention is suitable for use in medicine and can be used in the treatment of immunological disorders and infections, particularly IgM deficiency disorder and bacterial infections. Human IgM-enriched polyvalent immunoglobulin preparation for intravenous administration, which can be prepared by the process of the present invention, contain higher antibody titres against clinically relevant Gram-negative and Gram-positive bacteria as well as higher antibody titres against endotoxins of Gram-negative bacteria and exotoxins of Gram-negative and Gram-positive bacteria compared with polyvalent immunoglobulin G preparations.

In particular, the antibody preparations of the present invention are suitable for intravenous administration to patients, and in particular are suitable for intravenous injection in humans.

The invention also provides a method of treatment of a patient comprising a step of administering the antibody preparation of the present invention to the patient. In particular, the patient can be suffering from an immunological disorder or a bacterial infection.

The present invention will now be described further by way of example only.

Description of the test method for determination of the anti-complementary activity The assay to determine the anti-complementary activity was carried out according to the method described in the European Pharmacopoeia (method 2.6.17, Ph. Eur. 6. Edition, 2008).

Hemolysin pre-treated sheep erythrocytes are hemolysed by complement. By complement-binding antibodies in the sample the hemolysis is suppressed. The amount of complement is determined, which is bound (inactivated) by 1 mg immunoglobulin.

A certain amount of immunoglobulin (10 mg) is mixed with complement of guinea pig and the free complement is titrated. The anti-complementary activity is expressed a used complement in respect to the used complement of a reference solution. The hemolytic unit of complement activity ($CH_{50}$) is the amount of complement leading to hemolysis of $2.5 \times 10^8$ optimally prepared erythrocytes of a total amount of $5 \times 10^8$ erythrocytes in optimal buffer conditions.

Optimally prepared erythrocytes (8 ml stabilized erythrocytes from sheep, washed three times with gelatine-barbital-buffer, finally 1 ml erythrocyte sediment are suspended in 24 ml gelatine-barbital-buffer) are prepared by mixing 20 ml erythrocytes suspension with 20 ml hemolysine (adjusted to 2 MHE/ml—minimal hemolytic unit) and incubation for 15 min at 37° C.

An equivalent of 10 mg immunoglobulin is diluted in gelatine-barbital-buffer (1 g gelatine in 1 L barbital buffer pH 7.3, 5-fold barbital-buffer solution: 83 g sodium chloride, 10.192 g sodium barbital in 2 liters water, pH 7.3). To a final volume of 1 ml 200 µl complement 100 $CH_{50}$/ml are added.

The test tubes are incubated under shaking for 1 h at 37° C. The samples are diluted and titrated against optimally prepared erythrocytes. After an incubation for 1 h at 37° C. the samples are centrifuged and the optical density is determined by using a spectrophotometer at a wavelength of 541 nm.

Example 1

Preparation of an IgM Enriched Preparation from Fraction I/III 180 kg Cohn Fraction I/III, originating from cold ethanol fractionation of human plasma are suspended in 720 L 0.1 M sodium acetate buffer pH 5.05 and mixed for 15-30 minutes after the suspension temperature is reached (22±4° C.).

The solution is treated by addition of a 19.8 kg octanoic acid (0.110 kg per kg paste I/III used) at room temperature and the protein solution is further mixed for 80 minutes, using a vibrating mixer (Vibromixer®, Size 4, Graber+Pfenniger GmbH, Vibromixer adjusted to level 2-3). The octanoic acid is added slowly over 30 min.

Approx. 3 kg tri-calcium phosphate ($Ca_3(PO_4)_2$) are added and the protein solution is further mixed for at least 15 min. The precipitate is removed by clarifying filtration using a filter press. An additional 0.2 µm filtration is carried out and the protein solution is subjected to ultrafiltration with 10 kD membranes. The protein solution is diafiltered against 0.04 M NaCl solution and afterwards adjusted to a protein concentration of 40 g/L.

The protein solution is treated at pH 4.0±0.1 after dilution 1+1 with water for injection. pH adjustment is carried out by using 1 M HCl and the protein solution is incubated for 9 h at 37° C.±2° C. After the pH 4 incubation the protein solution is adjusted to pH 5.8, using 1 M NaOH. The resulting protein solution is further purified by adding DEAE Sephadex in a batch mode (75 g DEAE Sephadex per kg protein). The protein solution is incubated under stifling for ≥60 min at room temperature. The DEAE Sephadex is removed by clarifying filtration. The protein solution is subjected to a 0.2 µm filtration.

The protein solution is filtered through a 0.1 µm filter and a Pall, Ultipor VF DV50, 20" filter. The filtrate is further processed by UVC light treatment at 254 nm, using a flow-through UVivatec® process device (Bayer Technology Services/Sartorius Stedim) at a UVC dose of 240 $J/m^2$. The flow velocity through the UVC reactor is calculated using the manufacture's instructions. The irradiated protein solution is concentrated to a protein concentration of 50-70 g/l by ultrafiltration and is subjected to diafiltration (10 kD membrane, using 0.32 M glycine buffer pH 4.3). The final product is filtered through a 0.2 µm filter and is stored at 2 to 8° C.

Example 2

Investigation of Conditions in Octanoic Acid Treatment Step

For the octanoic acid treatment the following experimental ranges were tested, also in combination with each other using the method described in Example 1 (results not shown).

Octanoic acid amount: 0.09 kg/kg to 0.13 kg/kg (Amount octanoic acid per kg used fraction I/III) (120 to 180 mM octanoic acid)

pH of the octanoic acid treatment between pH 4.8 and 5.3
Temperature range of the reaction: 14° C. to 30° C.
Incubation time: 40 to 110 min All conditions tested lead to intermediates being easy to clarify for further processing and with a extensive reduction of proteolytic activity from several thousand U/L in suspended Cohn fraction I/III). These intermediates result in a final product with a proteolytic activity below 8 U/l (calculated as described below in Example 6) which is the limit of quantitation.

Example 3

Virus Reduction Through Use of Vibromixer—Determination of Virus Removal Factors for the Octanoic Acid Treatment with and without Use of a Vibromixer 250 ml of suspended faction I/III were homogenised for 30 min at pH 5.05 and 22° C. The suspension was spiked with 2.6 ml of the virus stock solution. Octanoic acid was added (110 g/kg) and homogenised for 60 min using a vibromixer. In a parallel experiment the same mixture was homogenised with standard stirring. After 60 min tri-calcium phosphate (0.15 g/kg octanoic acid) was added and the suspension stirred for 15 min. The suspension was cleared by depth filtration using a filter disc. The filter disc was pre-rinsed with 70-80 ml of buffer. After filtration, the filter was rinsed with 80 ml of buffer. Filtrate and wash were pooled and a sample was drawn for virus titration.

Virus titres from samples taken prior to addition of octanoic acid and after filtration were determined on appropriate indicator cells for SV40, Reo and PPV (CV-1, CCL.7.1 and PK13). Finally, the removal factor was calculated in compliance with the current guidelines for virus validation studies.

In virus validations studies, non-enveloped viruses such as SV40 and Reo were effectively removed in the order of more than 4 $log_{10}$ and more than 5 $log_{10}$, respectively. Moreover, PPV was removed by more than 3 $log_{10}$. These values are more than 10 times and up to 1000 times higher than with the same octanoic acid treatment under standard stirring conditions without vibromixing.

TABLE 1

Comparison of the virus reduction factors ($log_{10}$) for the octanoic acid treatment with and without the use or a vibromixer.

|  | Octanoic acid reaction standard stirring [$log_{10}$ reduction] | Octanoic acid reaction with vibromixing [$log_{10}$ reduction] |
|---|---|---|
| PPV | 2.15 ± 0.32 | 3.39 ± 0.36 |
| REO | 2.34 ± 0.38 | 5.46 ± 0.28 |
| SV40 | 2.05 ± 0.4 | 4.71 ± 0.34 |

Example 4

Evaluation of UVC Treatment

The optimal range for the dosage of UVC radiation has been evaluated. There is a balance between the minimal necessary dosage to achieve at least 4 $log_{10}$ inactivation for non enveloped viruses and the maximum tolerable dosage to avoid denaturation of the IgM molecules leading to an impaired Fab function to bind antigens and impaired Fc function influencing complement activation. In the range of 200 to 400 $J/m^2$ one could observe only a slight increase of immunoglobulin aggregates and no significant impact on fragment content.

For the experiments the optical density (OD) of the original protein solution is used to calculate the flow rate in the UVivatec lab system with the vendor provided Excel-Sheet from BTS (customer Master Calculation Sheet UVivatec Lab II Version 3.0). The flow rate is calculated by taking into account the lamp performance, the set point of the UV signal lamp sensor and the desired UVC irradiation dose.

IgM containing solution with a protein content of about 55 g/l (Batch 86GB005BE07) was pumped at a flow rate of 5.8 l/h through the UVivatec system in order to achieve a dose of 200 J/m$^2$ for a single flow-through. A dose of 300 J/m$^2$ was achieved by pumping the protein solution at a flow rate of 3.9 L/m$^2$ through the system. 400 J/m$^2$ were achieved by pumping the protein solution at a flow rate of 2.9 L/m$^2$ through the system.

TABLE 2

Analytical results for the activity and titre determinations before and after UVC treatment in the concentrated final product

|  |  | IgM product no UVC-irradiation | IgM product after UVC 200 J/m$^2$ | IgM product after UVC 300 J/m$^2$ | IgM product after UVC 400 J/m$^2$ |
|---|---|---|---|---|---|
| Protein content | g/l | 56.3 | 56.2 | 57.6 | 54.4 |
| IgG content (nephelometry) | % | 56.1 | 55.5 | 55.7 | 54.9 |
| IgA content (nephelometry) | % | 20.1 | 20.6 | 20.5 | 20.7 |
| IgM content (nephelometry) | % | 23.7 | 23.9 | 23.7 | 24.4 |
| HPSEC |  |  |  |  |  |
| aggregates > 1200 kD | area % | 1.9 | 2.6 | 3.3 | 4.0 |
| fragments < 100 kD | area % | 0.66 | 0.73 | 0.76 | 0.79 |
| ACA | CH50/mg protein | 0.68 | 0.48 | 0.46 | 0.46 |
| PA | U/l | <8 | <8 | <8 | <8 |

No significant difference could be observed for immunoglobulin content, proteolytic activity or ACA in the range of 200 to 400 J/m$^2$. The preferred range for the dosage was set between 200 and 300 J/m$^2$ because 200 J/m$^2$ are well enough to inactivate non enveloped viruses and at 300 J/m$^2$ no significant impact could be seen on aggregate formation and antibody titres. The preferred dosage is 225 J/m2

Diluted IgM containing solution with a protein content of 8 to 12 g/l (Batch 86BB059BE07) was pumped at a flow rate of 5.8 l/h through the UVivatech system in order to achieve a doses between 200 and 300 J/m$^2$ for a single flow-through.

TABLE 3

Analytical results for IgM solutions before and after UVC irradiation at different UVC doses

| | | Batch fraction I/III 86BB059BE07 | | | | |
|---|---|---|---|---|---|---|
| | | before UVC | UVC: 200 J/m$^2$ | UVC: 225 J/m$^2$ | UVC: 250 J/m$^2$ | UVC: 300 J/m$^2$ |
| Protein | g/l | 11.34 | 10.56 | 10.65 | 10.69 | 10.56 |
| IgG content | % | 59.2 | 59.1 | 58.5 | 58.6 | 57.1 |
| IgA content | % | 19.6 | 19.6 | 20.2 | 20.1 | 20.3 |
| IgM content | % | 21.1 | 21.3 | 21.2 | 21.4 | 22.6 |
| HSEC | | | | | | |
| aggregates > 1200 kD | % | 0.20 | 0.39 | 0.54 | 0.3 | 0.47 |
| fragments < 100 kD | % | 0.47 | 0.46 | 0.25 | 0.26 | 0.47 |
| PA | U/l | <8 | <8 | n.t. | n.t. | n.t. |
| PKA | U/ml | 3 | 3 | 3 | 3 | 3 |
| ACA | CH50/mg protein | 0.1 | 0.08 | 0.1 | 0.1 | 0.18 |
| Anti-*E. coli* O1:K1 - IgG | U/mg | 24.7 | 20.5 | 18.9 | 19.5 | 20.2 |
| Anti-*E. coli* O1:K1 - IgA | U/mg | 9.4 | 9.5 | 9.5 | 9.1 | 8.9 |
| Anti-*E. coli* O1:K1 - IgM | U/mg | 14.1 | 13.0 | 15.1 | 13.9 | 13.4 |
| Anti-*Candida albicans* - IgG | U/mg | 15.6 | 16.8 | 17.9 | 17.3 | 17.0 |
| Anti-*Candida albicans* - IgA | U/mg | 11.3 | 11.6 | 10.5 | 10.3 | 10.4 |
| Anti-*Candida albicans* - IgM | U/mg | 13.8 | 13.3 | 13.7 | 13.9 | 13.1 |
| Anti-*Enterococcus faecalis* - IgG | U/mg | 13.0 | 15.5 | 13.5 | 14.8 | 15.0 |
| Anti-*Enterococcus faecalis* - IgA | U/mg | 11.3 | 10.5 | 10.1 | 9.7 | 9.6 |
| Anti-*Enterococcus faecalis* - IgM | U/mg | 17.2 | 14.1 | 16.7 | 14.0 | 13.9 |
| Anti-*Pneumococcus* Saccharid -IgG | U/mg | 23.2 | 24.1 | 24.7 | 24.0 | 25.7 |
| Anti-*Pneumococcus* Saccharid -IgA | U/mg | 13.3 | 12.1 | 18.0 | 16.5 | 14.8 |
| Anti-*Pneumococcus* Saccharid -IgM | U/mg | 17.5 | 15.1 | 18.0 | 16.4 | 16.6 |

The distribution between the immunoglobulin classes remains unaffected by the UV irradiation within this dosage range procedure. The molecular weight distribution pattern analyzed by HPSEC is also not changed. The level of purity analyzed by CZE remains unchanged. Proteolytic activity (PA), prekallikrein activator (PKA) and anti-complementary activity (ACA) are unchanged. Also the anti bacterial activity measured by an Elisa method are not significantly altered for all immunoglobulin classes.

The aliquots—irradiated with increasing UV intensities—were further processed until final product and subjected to the same panel of analytical tests. There was also no significant difference observable in the final products. All tested antibody titres are always in the range of 100±10% of the control preparation not UVC treated.

Example 5

Overall Virus Reduction Through Use of Vibromixer/pH4 Treatment and UVC Treatment—Determination of Virus Removal Factors The validation of virus removal/inactivation of the three steps octanoic acid treatment with vibromixing, pH4 treatment and UVC treatment (215 J/m$^2$) was performed using the following model viruses: Bovine Viral Diarrhea Virus (BVDV) as model virus for Hepatitis C Virus, Pseudorabies Virus (PRV) as model virus for Human Herpes Viruses, Human Immunodeficiency virus (HIV-1), Equine Arteritis Virus (EAV) as model virus for corona viruses, Sindbis Virus (SinV) as model virus for Flavi viruses, Murine Encephalomyelitis Virus (MEV) as model virus for Hepatitis A Virus, Reovirus (Reo) as model virus for other non enveloped viruses, Porcine Parvovirus (PPV) as model virus for human Parvovirus B19.

The results of these studies with the three steps octanoic acid treatment, pH4 treatment and UVC treatment are listed in the following Table 2.

TABLE 4

Total virus reduction by the IgM production process

| | Model virus | | | | | | | |
|---|---|---|---|---|---|---|---|---|
| | BVDV | PRV | HIV-1 | EAV | SinV | MEV | Reo | PPV |
| Total reduction (log$_{10}$) | >12.5 | >10.1 | >12.7 | >8.4$^a$ | >13.7$^a$ | 9.2 | >11.0 | >8.4 |

$^a$Reduction factor without data for validation of the UVC irradiation step

The optional nano filtration with filters with a nominal pore size of about 50 nm adds additional safety by increasing the total reduction up to more than 17 log 10 depending on the size of the virus. E.g >17.5 log$_{10}$ are then reached for HIV-1 whereas PPV was not further removed by nano filtration.

Therefore the purification procedure according to the invention leads to an outstanding virus safe IgM preparation with up to now for such an IgM containing preparation unreached virus inactivation/reduction rates of more than 8 log$_{10}$. This is especially important for the non enveloped viruses like MEV, Reo and PPV which are generally more resistant against virus inactivation and removal procedures due to their small size and the lack of a lipid envelope.

Example 6

Determination of Residual Proteolytic Activity for the Octanoic Acid Treatment with and without Use of a Vibromixer The octanoic acid treatment was performed like in example 1 and in a parallel experiment without a vibromixer but with vigorous standard stifling with a blade stirrer. The proteolytic activity in samples after octanoic acid/tricalcium phosphate treatment and ultra-/diafiltration were determined using the chromogenic substrate S-2288 (Chromogenix), following the manufacturers instructions.

25 mg of the substrate S-2288 (Chromogenix) are dissolved in 7.2 ml water-for-injection. Samples are diluted into buffer (100 mM Tris/HCl pH 8.4, 106 mM NaCl) to meet the linear range of the assay, e.g. 200 μl buffer are mixed with 200 μl sample (mixing and temperature adjustment to 37° C.) and 200 μl chromogenic substrate solution. The absorption kinetics are measured at 405 nm (1-3 min) at 37° C., using a spectrophotometer. The proteolytic activity of the sample is calculated from the initial absorption difference (ΔAbs/min) by using the equation C (U/L)=313*ΔAbs/min*F (C=proteolytic activity, F=dilution factor)

TABLE 5

Reduction of proteolytic activity by octanoic acid treatment

| | Octanoic acid treatment without vibromixing | Octanoic acid treatment with vibromixing |
|---|---|---|
| Starting material (U/l) | 5630 | 5630 |
| Mean residual proteolytic activity after octanoic acid treatment (U/L) | 42 | <8 (LOD) |

The filtrate after octanoic acid treatment was limpid when vibromixing was employed. In the comparison experiment the filtrate after octanoic acid treatment with blade stirrer was very opaque and difficult to filtrate.

Example 7

Anti-Bacterial Titres in an IgM Preparation According to the Invention

For comparison with the only commercially available intravenous tolerable IgM containing preparation, Pentaglobin, the anti-bacterial activities were analyzed in three batches of this well established drug and compared to a preparation according to the invention. The determination of antibodies of the IgA or IgM class in the IgM preparation versus antibacterial or antifungal antigens was carried out by ELISA. Microtitre plates were coated with a corresponding antigen and incubated with a standard or the IgM preparation.

Antibodies bound to the antigen were detected with an anti-human-IgA or anti-human-IgM conjugate. The detection was carried out by using an enzyme substrate. The resulting colour change is corresponding to the amount of antibodies present in IgM preparation.

TABLE 6

Comparison of anti bacterial binding activity of IgM in an preparation according to the invention and commercially available Pentaglobin

| parameter | unit | IgM preparation invention mean | Pentaglobin commercial product mean |
|---|---|---|---|
| IgM antibodies against Pneumococcus saccharide | U/mg IgM | 72 | 21 |
| IgM antibodies against Escherichia coli | U/mg IgM | 62 | 39 |
| IgM antibodies against Enterococcus faecalis | U/mg IgM | 69 | 27 |
| IgM antibodies against Candida albicans | U/mg IgM | 61 | 41 |
| IgM antibodies against Chlamydia | U/mg IgM | 71 | 6 |

TABLE 7

Comparison of anti bacterial binding activity of IgA in an preparation according to the invention and commercially available Pentaglobin

| parameter | unit | IgM preparation invention mean | Pentaglobin commercial product mean |
|---|---|---|---|
| IgA antibodies against Pneumococcus saccharide | U/mg IgA | 86 | 25 |
| IgA antibodies against Escherichia coli | U/mg IgA | 83 | 26 |
| IgA antibodies against Enterococcus faecalis | U/mg IgA | 93 | 21 |
| IgA antibodies against Chlamydia | U/mg IgA | 65 | 38 |
| IgA antibodies against Helicobacter pylori | U/mg IgA | 59 | 24 |

The IgM and IgA mediated activities in the new preparation were typically at least 1.5 times as high as in Pentaglobin which can be explained by the fact that IgM and IgA in Pentaglobin is chemically modified with β-Propiolactone This step is replaced by the more gentle procedures according to this invention.

Overall these data demonstrate that the binding region of the IgM molecules in the final preparation is functionally full active.

Example 8

Storage Stability Studies with Liquid IgM Product

Product according example 1 without UVC treatment was stored in 10 or 100 ml glass vials (filling volume 5 ml or 50 ml) at 2-8° C. and analyzed for all parameter according to specification. The results are shown in Table 8. Parameter which are relevant to show stability are the aggregate and fragment content measured with high performance size exclusion chromatography (HPSEC), proteolytic activity (PA) and anticomplementary activity (ACA). These parameter are critical for intravenous tolerability and likely to change during long term storage. At 2-8° C. there was no significant change of these parameters. Even at storage at room temperature (23-27° C.) these values remained within specification, although there is a slight increase of fragments after 24 months at room temperature. Other parameter like coloration, opalescence, pH value were also determined and stayed unchanged over the whole study period. IgM and IgA titres against various bacteria remain stable over 2 years at 2-8° C.

Product according example 1 with UVC treatment was also stored in 10 or 100 ml glass vials (filling volume 5 ml or 50 ml) at 2-8° C. and room temperature and analyzed for all parameter according to specification. The results are shown in Table 9. In this ongoing stability study the currently available 12 month date show the same stability profile of the product as without UVC treatment which allows the extrapolation to a 24 month stability.

TABLE 8

Stability of the batch A586067 tested at 2-8° C. lying position Filling size: 5 ml

| Parameters tested | Requirement (Tolerance) | Storage in months 2-8° C. | | | | | | | 23-27° C. |
|---|---|---|---|---|---|---|---|---|---|
| | | 0 | 3 | 6 | 9 | 12 | 18 | 24 | 24 |
| protein (g/l) | 45-55 | 50.3 | 51.4 | 50.3 | 50.4 | 50.5 | 49.6 | 50.8 | 49.8 |
| HPSEC | | | | | | | | | |
| % aggregates > 1200 kD | ≤5 | 0.9 | 0.6 | 0.5 | 0.8 | 0.6 | 1.0 | 1.3 | 1.7 |
| % fragments < 100 kD | ≤5 | 0.2 | 0.6 | 1.1 | 0.7 | 1.6 | 0.9 | 1.2 | 4.1 |
| proteolytic activity (U/l) | <8 | <8 | <8 | <8 | n.t. | <8 | n.t. | <8 | <8 |
| immunoglobulin content (%) | >95% | 96.7 | 99.0 | 100 | n.t. | 99.5 | n.t. | 98.4 | 97.5 |
| IgM content | ≥20% | 21.6 | 22.1 | 22.1 | n.t. | 22.3 | n.t. | 20.9 | 20.5 |
| anticomplementary activity (CH50/mg protein) | ≤1.0 | 0.48 | 0.56 | 0.48 | 0.66 | 0.70 | 0.64 | 0.54 | 0.38 | n.t. = not tested

TABLE 9

Stability of the batch A586057 tested at 2-8° C. lying position Filling size: 50 ml

| Parameters tested | Requirement (Tolerance) | Storage in months 2-8° C. | | | | | | | 23-27° C. |
|---|---|---|---|---|---|---|---|---|---|
| | | 0 | 3 | 6 | 9 | 12 | 18 | 24 | 24 |
| protein (g/l) HPSEC | 45-55 | 50.2 | 50.8 | 49.7 | 50.4 | 50.3 | 49.4 | 50.3 | 49.7 |
| % aggregates > 1200 kD | ≤5 | 0.9 | 0.5 | 0.4 | 0.8 | 0.6 | 1.0 | 1.3 | 1.5 |
| % fragments < 100 kD | ≤5 | 0.3 | 0.6 | 1.0 | 0.9 | 1.4 | 1.2 | 1.2 | 4.2 |
| proteolytic activity (U/l) | <8 | <8 | <8 | <8 | n.t. | <8 | n.t. | <8 | <8 |
| immunoglobulin content (%) | >95% | 98.6 | 98.9 | 100 | n.t. | 99.5 | n.t. | 98.5 | 98.0 |
| IgM content | ≥20% | 21.3 | 22.3 | 24.5 | n.t. | 22.0 | n.t. | 20.9 | 20.1 |
| anticomplementary activity (CH50/mg protein) | ≤1.0 | 0.48 | 0.82 | 0.52 | 0.64 | 0.68 | 0.48 | 0.60 | 0.40 |

Example 9

In Vivo Experiments with IgM Product

To confirm safety and tolerability the effects of the IgM preparation on arterial blood pressure following repeated intravenous infusions over 5 days were studied in 8 conscious cynomolgus monkeys. A dose of 190 mg/IgM/kg/day of the IgM preparation prepared according to the methods described herein was administered. Pentaglobin, the commercially available intravenous tolerable IgM containing preparation was administered to some monkeys as a comparison substance. Pentaglobin was administered in such a way that the same IgM dose was administered. A control dose of 0.9% NaCl was administered to the animals sometime prior to the administration of the immunoglobulin preparations. Blood pressure was determined following injection to determine whether administration was associated with an intolerable level of non-specific complement activation.

The administration of the IgM preparation (15 ml/kg/day) had only minor effects on arterial blood pressure (mean, systolic and diastolic). The differences up to 4 hourse after every infusion compared to pretest values did not exceed 4 mmHg. These differences can be considered not biologically relevant.

C3a levels were determined in plasma samples taken after injection as a marker for unspecific activation of the complement pathway. C3a levels [ng/ml] were only slightly increased by the administration of the IgM preparation (15 mL/kgBW) and were even lower than with the commercially available reference preparation Pentaglobin at equal amounts of IgM. Blood samplings were performed approximately 6 hours after treatment.

TABLE 10a

C3a levels [ng/ml] after the administration of the IgM preparation

| | Control (0.9% NaCl, pH 4.5) C3a [ng/ml] | Administration of IgM preparation C3a [ng/ml] |
|---|---|---|
| Mean | 229 | 240 |
| SD | 83 | 37 |
| N | 8 | 8 |

No substantial toxicological findings could be attributed to the IgM preparation, and there were no relevant alterations that have not been observed with Pentaglobin. As the safety of Pentaglobin is well established in the clinical practice of many years it is reasonable to conclude that these alterations do not have any clinical relevance.

TABLE 10b

C3a levels [ng/ml] after the administration of the reference preparation Pentaglobin

| | Control (0.9% NaCl, pH 6.8) C3a [ng/ml] | Administration of IgM preparation C3a [ng/ml] |
|---|---|---|
| Mean | 204 | 263 |
| SD | 20 | 61 |
| N | 4 | 4 |

The good tolerability and safety of the IgM preparation was also verified in a human Phase I study in 24 healthy male and female volunteers. Systolic blood pressure in the first 4 hours after administration in the mean decreased only about 9% (11.9 mmHg) after infusion of 91 to 274 mg of the IgM preparation per kg BW/d at 0.5 ml/min.

This was in the same range like the placebo 0.9% NaCl-solution (9.4%, 11.7 mmHg).

No serious advsere events were recorded and all non-serious adverse events were self limiting. Further, there was no evidence for the transmission of an infectious agent, as shown by PCT determinations.

It is noted that the usefulness of efficacy studies in animal models of relevant diseases is limited due to the immunogenicity and preformed Gal-antibodies in IgM preparations obtained from human plasma. However, given the prior art knowledge regarding the use of Pentaglobin in the treatment of disease and the anti-bacterial antibody titres of the IgM preparation prepared by the method of the present invention (as demonstrated in Example 7) it can be concluded that the IgM preparation have clinical efficacy.

We claim:

1. A process for the preparation of an IgM-containing immunoglobulin composition from a plasma fraction including immunoglobulins, the process comprising:
    (a) providing a plasma fraction as a solution containing the immunoglobulins;
    (b) mixing a $C_7$ to $C_9$ carboxylic acid with the solution, wherein the resulting mixed solution has a temperature of 10° C. to 35° C.;
    (c) agitating the mixed solution with a vibrating agitator to precipitate contaminating proteins; and
    (d) separating the precipitated contaminating proteins from the solution to yield the IgM-containing immunoglobulin composition.

2. A process according to claim 1 wherein in step (b) the concentration of the $C_7$ to $C_9$ carboxylic acid is at least 0.075 kg/kg of plasma fraction.

3. A process according to claim 1 wherein in step (b) the pH of the mixed solution is between 4.5 to 5.5.

4. A process according to claim 1 wherein in step (b) the $C_7$ to $C_9$ carboxylic acid is incubated with the solution containing immunoglobulins for at least 30 minutes.

5. A process according to claim 1 wherein the $C_7$ to $C_9$ carboxylic acid is octanoic acid.

6. A process according to claim 1 wherein the immunoglobulins of the plasma fraction comprise at least 5% IgM.

7. A process according to claim 1 wherein the plasma fraction is a precipitation of Cohn fraction I/III or Kistler/Nitschmann fraction B or B+I.

8. A process according to claim 1 wherein step (d) comprises ultrafiltration and the immunoglobulin composition comprises a filtered solution.

9. A process according to claim 1 further comprising:
incubating the IgM containing immunoglobulin composition from step (d) at between pH 3.5 and pH 4.5 to form an incubated solution.

10. A process according to claim 9 wherein said step of incubating is conducted at between 32° C. and 42° C.

11. A process according to claim 9 further comprising:
subjecting the incubated solution to adsorption on DEAE-Sephadex; and
separating the DEAE Sephadex from the solution by depth filtration to form a filtrate.

12. A process according to claim 11 further comprising:
subjecting the filtrate from the depth filtration to nanofiltration.

13. A process according to claim 12 wherein the nanofiltration is conducted with a filter with a 35 to 75 nm nominal pore size and preferably a 40 to 50 nm nominal pore size.

14. A process according to claim 9 further comprising:
treating the incubated solution with UVC irradiation to form a UVC irradiated solution.

15. A process according to claim 14 wherein said step of treating the incubated solution with UVC irradiation comprises treating with UVC irradiation at 200 to 500 $J/m^2$.

16. A process according to claim 14 wherein said step of treating the incubated solution with UVC irradiation comprises treating with UVC irradiation at 200 to 300 $J/m^2$.

17. A process according to claim 14 further comprising:
filtering the UVC irradiated solution under sterile conditions to produce an antibody preparation suitable for intravenous administration.

18. A process according to claim 17 further comprising:
performing at least said steps (b), (c), and (d) in a glycine-containing buffer at a pH between pH 4 and 5.5.

19. A process according to claim 14 further comprising:
filling a container with the UVC irradiated solution under sterile conditions.

20. A process according to claim 14 wherein the UVC irradiated solution has a proteolytic activity of less than 8U/l.

21. A process according to claim 14 which provides a more than 3 $\log_{10}$ removal of non-enveloped viruses.

* * * * *